US011141130B2

(12) United States Patent
Tanter et al.

(10) Patent No.: US 11,141,130 B2
(45) Date of Patent: Oct. 12, 2021

(54) INSONIFICATION METHOD FOR OBTAINING A PREDETERMINED FIELD OF ULTRASONIC WAVES AND PRODUCTION METHOD FOR MAKING AN ULTRASONIC LENS FOR THESE PURPOSES

(71) Applicants: CENTRE NATIONAL DE LA RECHERCHE SCIENTIFIQUE—CNRS, Paris (FR); INSERM (INSTITUT NATIONAL DE LA SANTÉ ET DE LA RECHERCHE MÉDICALE), Paris (FR)

(72) Inventors: Mickaël Tanter, Bagneux (FR); Jean-François Aubry, Bourg la Reine (FR); Thomas Deffieux, Cergy (FR); Mathieu Pernot, Paris (FR)

(73) Assignees: CENTRE NATIONAL DE LA RECHERCHE SCIENTIFIQUE (CNRS), Paris (FR); INSERM (INSTITUT NATIONAL DE LA SANTÉ ET DE LA RECHERCHE MEDICALE), Paris (FR)

( * ) Notice: Subject to any disclaimer, the term of this patent is extended or adjusted under 35 U.S.C. 154(b) by 679 days.

(21) Appl. No.: 15/740,727

(22) PCT Filed: Jun. 30, 2016

(86) PCT No.: PCT/FR2016/051625
§ 371 (c)(1),
(2) Date: Dec. 28, 2017

(87) PCT Pub. No.: WO2017/001781
PCT Pub. Date: Jan. 5, 2017

(65) Prior Publication Data
US 2018/0192990 A1    Jul. 12, 2018

(30) Foreign Application Priority Data

Jul. 1, 2015    (FR) ...................................... 15 56217

(51) Int. Cl.
*B06B 3/04*    (2006.01)
*A61B 8/00*    (2006.01)
(Continued)

(52) U.S. Cl.
CPC .......... *A61B 8/0808* (2013.01); *A61B 8/4272* (2013.01); *B06B 3/04* (2013.01); *B29D 11/00* (2013.01); *G10K 11/30* (2013.01)

(58) Field of Classification Search
CPC .......... G10K 11/30; G10K 11/18; B06B 3/04; B06B 3/00; A61B 8/00; A61B 8/08;
(Continued)

(56) References Cited

U.S. PATENT DOCUMENTS 3,687,219 A  *  8/1972  Langlois ................ G10K 11/30
                                                    181/176
5,640,961 A      6/1997  Verdonk
(Continued)

FOREIGN PATENT DOCUMENTS

FR         2843874 A1        3/2004
WO    WO 2004/019784         3/2004
(Continued)

OTHER PUBLICATIONS

KIM et al., Rapid Prototyping Fabrication of Focused Ultrasound Transducers, 2014, IEEE Transactions on Ultrasonics, Ferroelectrics, and Frequency Control, vol. 61, No. 9, pp. 1559-1574 (Year: 2014).*

(Continued)

*Primary Examiner* — Edgardo San Martin
(74) *Attorney, Agent, or Firm* — Osha Bergman Watanabe & Burton LLP

(57) ABSTRACT

In order to obtain a predetermined ultrasonic wave field in a homogeneous internal part of a medium masked by an aberrating barrier, an ultrasonic lens is interposed between the emitting ultrasonic probe and the aberrating barrier. The ultrasonic lens is calculated by using a model of the medium comprising a mapping of ultrasonic wave propagation properties obtained from actual imaging of the medium such that when the ultrasound probe sends a predetermined ultrasonic wave, said predetermined wave generates the predetermined objective ultrasonic wave field in the medium.

17 Claims, 4 Drawing Sheets

(51) Int. Cl.
| | |
|---|---|
| *A61B 8/08* | (2006.01) |
| *A61N 7/00* | (2006.01) |
| *G10K 11/30* | (2006.01) |
| *B29D 11/00* | (2006.01) |

(58) Field of Classification Search
CPC ........... A61B 8/15; A61B 8/4272; A61B 8/44; A61B 8/4483; A61B 8/4494; A61N 7/00; A61N 2007/006
See application file for complete search history.

(56) References Cited

U.S. PATENT DOCUMENTS

| | | | |
|---|---|---|---|
| 2008/0189932 A1 | 8/2008 | Sliwa et al. | |
| 2018/0064960 A1* | 3/2018 | Kim | A61B 90/11 |

FOREIGN PATENT DOCUMENTS

| | | |
|---|---|---|
| WO | WO 2008/051473 | 5/2008 |
| WO | WO 2013/046080 | 4/2013 |
| WO | WO 2014176483 A1 | 10/2014 |

OTHER PUBLICATIONS

International Search Report related to Application No. PCT/FR2016/051625 dated Oct. 5, 2016.
Ralph E. Beard et al: "An annular focus ultrasonic lens for local hyperthermia treatment of small tumors" Received Jan. 6, 1981; in final form Jun. 18, 1981—Ultrasound in Med. & Biol. vol. 8, No. 2, pp. 177-184, 1982 printed in Great Britain.
Y. Kim et al. "Rapid Prototyping Fabrication of Focused Ultrasound Transducers" IEEE Transactions On Ultrasonics, Ferroelectrics, and Frequency Control, vol. 61, No. 9; Sep. 2014 (16 pages).
C. Song et al. "Liquid acoustic lens for photoacoustic tomography" Optics Letters, Optical Society of America, vol. 38, No. 15; Aug. 1, 2013 (4 pages).
A. Chan et al. "An image-guided high intensity focused ultrasound device for uterine fibrosis treatment" Medical Physics, vol. 29, No. 11; Nov. 2002 (10 pages).
P. Maréchal "Lens-focused transducer modeling using an extended KLM model" Ultrasonics vol. 46; Apr. 29, 2007 (13 pages).
A. E. Özøam "Effect of ultraviolet/ozone treatment on the surface and bulk properties of poly(dimethyl siloxane) and poly(vinylmethyl siloxane) networks" Polymer No. 55; May 17, 2014 (13 pages).
R. J. Lalonde et al. "Field Conjugate Acoustic Lenses for Ultrasound Hypothermia" IEEE Transactions on Ultrasonics, Ferroelectrics, and Frequency Control, vol. 40, No. 5; Sep. 1993 (11 pages).
T. Fjield et al. "Low-profile lenses for ultrasound surgery" Physics in Medicine and Biology vol. 44; Jan. 1999 (11 pages).

* cited by examiner

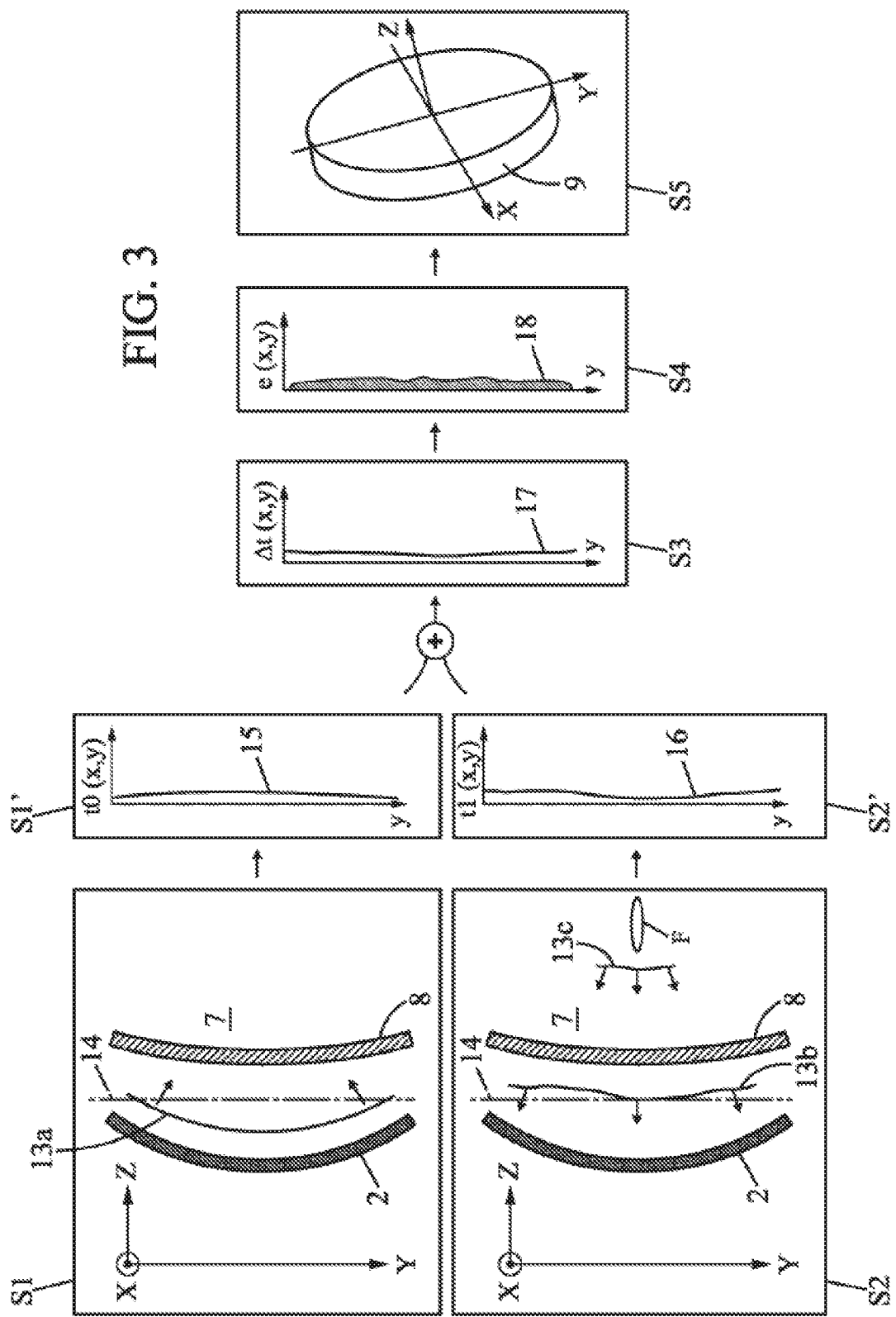

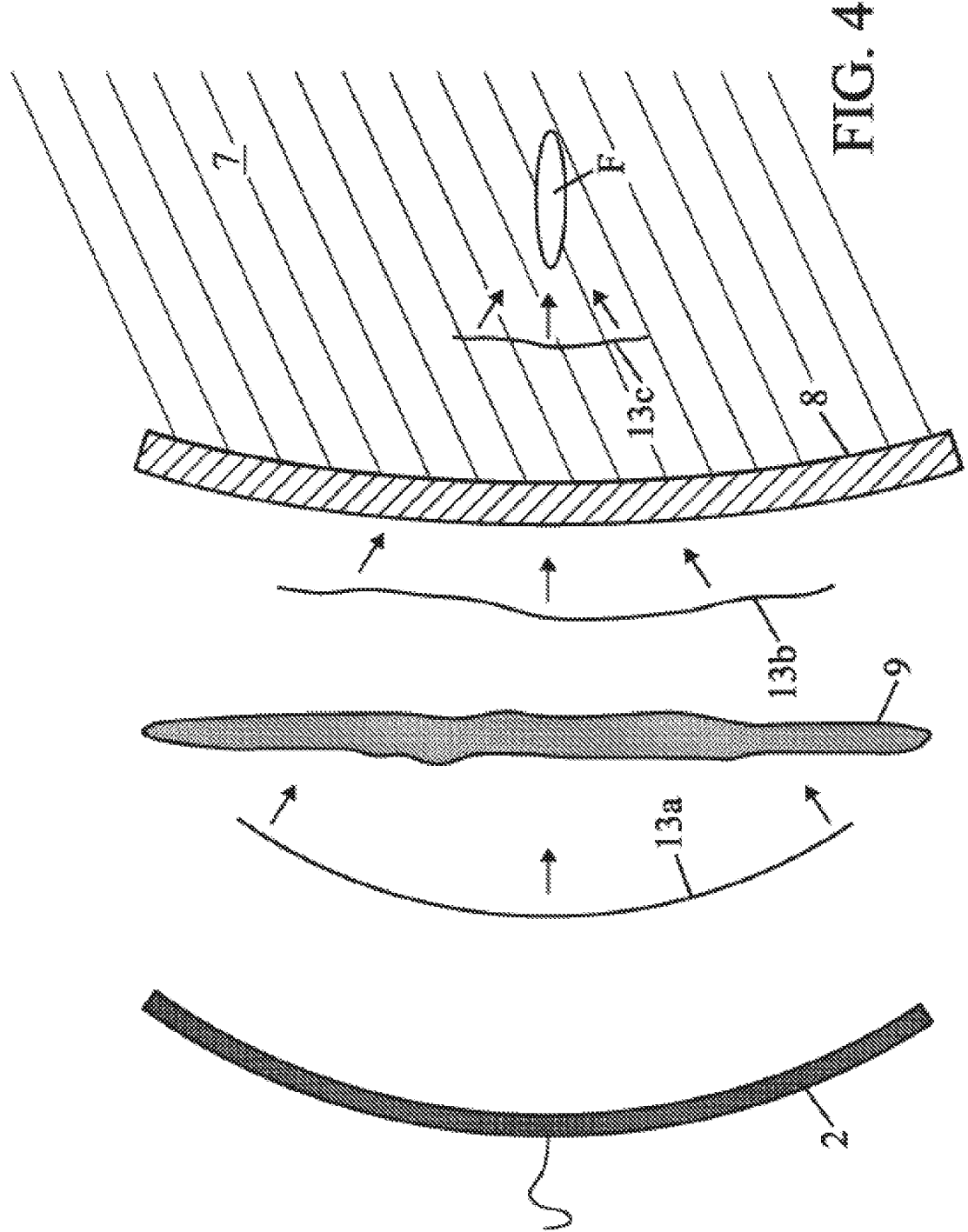

INSONIFICATION METHOD FOR OBTAINING A PREDETERMINED FIELD OF ULTRASONIC WAVES AND PRODUCTION METHOD FOR MAKING AN ULTRASONIC LENS FOR THESE PURPOSES

CROSS-REFERENCE TO RELATED APPLICATION

This Application is a 35 USC § 371 US National Stage filing of International Application No. PCT/FR2016/051,625 filed on Jun. 30, 2016, and claims priority under the Paris Convention to French Patent Application No. 15 56217 filed on Jul. 1, 2015.

FIELD OF THE DISCLOSURE

The present invention relates to methods for insonification for obtaining a predetermined field of ultrasonic waves in a substantially homogeneous medium masked by an osseous barrier, and production methods for implementing ultrasonic lenses for these purposes.

BACKGROUND OF THE DISCLOSURE

More specifically, the invention relates to an insonification method for obtaining, from an ultrasound probe, a predetermined objective field of ultrasonic waves in a medium comprising a substantially homogeneous internal part masked by at least one aberrating barrier, where the method comprises a step of simulation during which at least one propagation of ultrasonic waves is simulated in the medium based on a mapping of ultrasonic wave propagation properties in the medium.

Here "substantially homogeneous part" is understood to mean a medium having substantially homogeneous properties for ultrasonic wave propagation. It can for example involve the brain of a human or animal, in which case the aberrating barrier is made up by the skull.

The document WO 2004/019784 A1 describes an example of such a process in which, from the aforementioned simulation, individual signals to be sent by each transducer are determined in order to obtain the objective field in the internal part of the medium. This method works well but in practice requires a large number of transducers (typically 500 to 1000) and complex electronics capable of individually driving each transducer.

The object of the present invention is in particular further improving this type of method, in particular in order to allow practicing it with simplified and less costly means.

For this purpose, the invention proposes an insonification method for a medium comprising at least one aberrating barrier and a substantially homogeneous internal part masked by said aberrating barrier, in order to obtain a predetermined objective ultrasonic wave field in at least one predetermined area belonging to said internal part, by having said ultrasonic waves sent by an ultrasound probe placed in a predetermined position relative to said medium, on the other side of said aberrating barrier from said internal part, where the insonification method comprises at least the following steps:

SUMMARY OF THE DISCLOSURE (c) a lens calculation step during which an ultrasonic lens is calculated, using a model of the medium comprising a mapping of ultrasonic wave propagation properties obtained from actual imaging of the medium, that is suited, when it is interposed between the ultrasound probe and the aberrating barrier, for generating aberrations such that when the ultrasound probe sends a predetermined ultrasonic wave (independent of the particular aberrating barrier), said predetermined wave generates said predetermined objective ultrasonic wave field in said predetermined area;

(d) a step of implementation of the lens calculated in the lens calculation step (c);

(e) a step of emission during which said predetermined ultrasonic wave is sent by said ultrasound probe through the ultrasonic lens disposed in said predetermined position.

Because of these arrangements, the objective ultrasonic wave field can be obtained very simply, possibly with a reduced number of transducers (possibly a single one). In particular, the insonification method according to the invention does not require sending a particularly complex waveform from the ultrasound probe, because the probe can send a particularly simple predetermined wave, for example always focused at a predetermined distance.

In that way, using an actual image of the medium such as an x-ray (CT) or MRI image, the ultrasonic lens can be quickly calculated by computer means and then this lens can also be quickly implemented, for example by computerized production means such as three-dimensional printing or numerically controlled machining. A standard ultrasound probe and control means that are also standard can then insonify the medium in a desired and customized way. The lens can be reused many times for the same medium 3 (for example for the same patient). The ultrasound probe and the means of control thereof are reusable for several media (for example for several patients), without change or reprogramming, because the emitted ultrasonic wave is a predetermined wave, independent of the aberrating barrier specific to each application (and notably specific to each patient in the context of a medical application).

The insonification method is thus made very easy to use and at low cost.

In the preferred embodiments of the insonification method according to the invention, use could further be made of one and/or the other of the following dispositions:

The lens calculation step (c) is preceded by an imaging step (a) during which said mapping is done;

The imaging step (a) is done by x-ray or MRI imaging;

Said cartography is done from bone density measurements;

The lens implementation step (d) is done by a method chosen among three-dimensional printing of the lens and numerically controlled machining of at least one block of material for forming the lens;

The lens implementation step (d) comprises the following substeps:

(d1) A substep of implementation of at least one mold done by a method chosen among three-dimensional printing of said at least one mold and numerically controlled machining of at least one block of material for forming said at least one mold;

(d2) A substep of molding in which said lens or at least one component of said lens is molded in said at least one mold;

The lens calculation step (c) is preceded by a simulation step (b) during which:

(b1) Propagation in the medium of the predetermined ultrasonic wave from, the ultrasound probe disposed at said predetermined position to a chosen position of the lens is calculated, and the first arrival times $t_0(x,y)$ of said predetermined ultrasonic wave to said chosen lens position are determined;

(b2) Back-propagation in the medium (3) of said predetermined objective ultrasonic wave field from the predetermined area to said chosen lens position is simulated;

(b3) Second arrival times $t_1(x,y)$ of said back-propagation of said predetermined objective ultrasonic wave field to said chosen lens position are determined;

(b4) A delay law $\Delta t(x,y)$ at said chosen lens position equal to the sum of the first arrival times $t_0(x,y)$ and second arrival times $t_1(x,y)$ is determined; And during the lens calculation step (c), the ultrasonic lens is calculated using said delay law $\Delta t(x,y)$, so that when the ultrasound probe sends said predetermined ultrasonic wave through said ultrasonic lens, said predetermined wave reproduces the desired wave field in the target area after passing through said aberrating barrier;

The first arrival times $t_0(x,y)$ and the second arrival times $t_1(x,y)$ are determined at different control points $M(x,y)$ belonging to a predetermined control surface located at said chosen lens location;

The control surface is located between the ultrasound probe and the aberrating barrier;

At the lens calculation step (c), an ultrasonic lens thickness $e(x,y)$ is calculated at each point $L(x,y)$ of the lens corresponding to a control point $M(x,y)$ with the following formula:

$$e(x,y)=e_0+\Delta t(x,y)/(1/c-1/c_1) \quad (3)$$

where:—c is the speed of the ultrasonic wave in the medium outside of the aberrating barrier;

$c_1$ the speed of the ultrasonic wave in the lens;

$e_0$ is a constant such that $e(x,y)$ has a has a value at each point of the lens that is positive and greater than a predetermined minimum thickness;

The ultrasonic wave is monochromatic and at the lens (9) calculation step (c), a lens thickness $e(x,y)$ is calculated at each point $L(x,y)$ of the lens corresponding to a control point $M(x,y)$ with the following formula:

$$e(x,y)=e_0+\Delta t(x,y)/(1/c-1/c_1), \text{modulo} T/(1/c-1/c_1).$$

where:—c is the speed of the ultrasonic wave in the medium outside of the aberrating barrier;

$c_1$ is the speed of the ultrasonic wave in the lens;

$e_0$ is a real number such that $e(x,y)$ has a has a value at each point of the lens that is positive and greater than a predetermined thickness;

T is the period of the ultrasonic wave;

The lens calculation step (c) considers travel times of said predetermined ultrasonic wave in the ultrasonic lens and angles of incidence of said predetermined ultrasonic wave at the surface of the ultrasonic lens;

The lens calculation step (c) considers all the propagation of said predetermined ultrasonic wave, including echoes between the ultrasound probe, the ultrasonic lens and the aberrating barrier, so that the ultrasonic energy transmission yield can be optimized in the predetermined zones;

The lens calculation step (c) is done iteratively in order to optimize the ultrasonic energy transmission yield in the predetermined area, using an analytic or numerical model;

The medium in which the ultrasonic waves propagate is a human or animal head, where the aberrating barrier is a skull and the internal part is a brain;

Said predetermined ultrasonic wave field is focused in said internal part in at least one predetermined area.

Further, the object of the invention is also a production method for implementing an ultrasonic lens for purposes of insonification of a medium comprising at least one aberrating barrier and a substantially homogeneous internal part masked by said aberrating barrier, in order to obtain a predetermined objective ultrasonic wave field in at least one predetermined area belonging to said internal part, by having said ultrasonic waves sent by an ultrasound probe placed in a position predetermined relative to said medium on the other side of said aberrating barrier from said internal part, The production method comprises at least one lens calculation step (c) during which an ultrasonic lens is calculated, using a model of the medium comprising a mapping of ultrasonic wave propagation properties obtained from actual imaging of the medium, that is suited, when it is interposed between the ultrasound probe and the aberrating barrier, for generating aberrations such that when the ultrasound probe sends a predetermined ultrasonic wave, said predetermined wave generates said predetermined objective ultrasonic wave field in said predetermined area.

In preferred embodiments of the production method according to the invention, use could further be made of one and/or the other of the following dispositions:

The production method further comprises a step (d) of implementation of the lens calculated in the lens calculation step (c);

The lens implementation step (d) is done by a method chosen among three-dimensional printing of the lens and digitally controlled machining of at least one block of material for forming the lens;

The lens implementation step (d) comprises the following substeps:

(d1) A substep of mold implementation done by a method chosen among three-dimensional printing of said at least one mold and numerically controlled machining of at least one block of material for forming said at least one mold;

(d2) A substep of molding in which said lens or at least one component of said lens (9) is molded in said at least one mold;

Advantageously, the lens is implemented of a material having acoustic wave propagation properties modifiable by exposure to a predetermined radiation;

During lens calculation step (c), the lens is calculated by determining local mechanical characteristics of acoustic wave propagation in said lens;

And the method comprises a step (d) of implementation of the lens during which said lens is locally exposed to said predetermined radiation for obtaining the local mechanical properties of acoustic wave propagation determined in lens calculation step (c).

Other features and advantages of the invention will become apparent during the following description of one of the embodiments thereof, given as a nonlimiting example, with reference to the attached drawings.

BRIEF DESCRIPTION OF THE DRAWINGS

In the drawings:

FIG. 3 is a drawing illustrating the mode for calculation of the acoustic lens usable in the mechanism from FIG. 1;

FIG. 4 is a drawing illustrating the operation of the mechanism from FIG. 1.

DETAILED DESCRIPTION OF THE DISCLOSURE

In the various figures, the same references designate identical or similar items.

Figure 1:
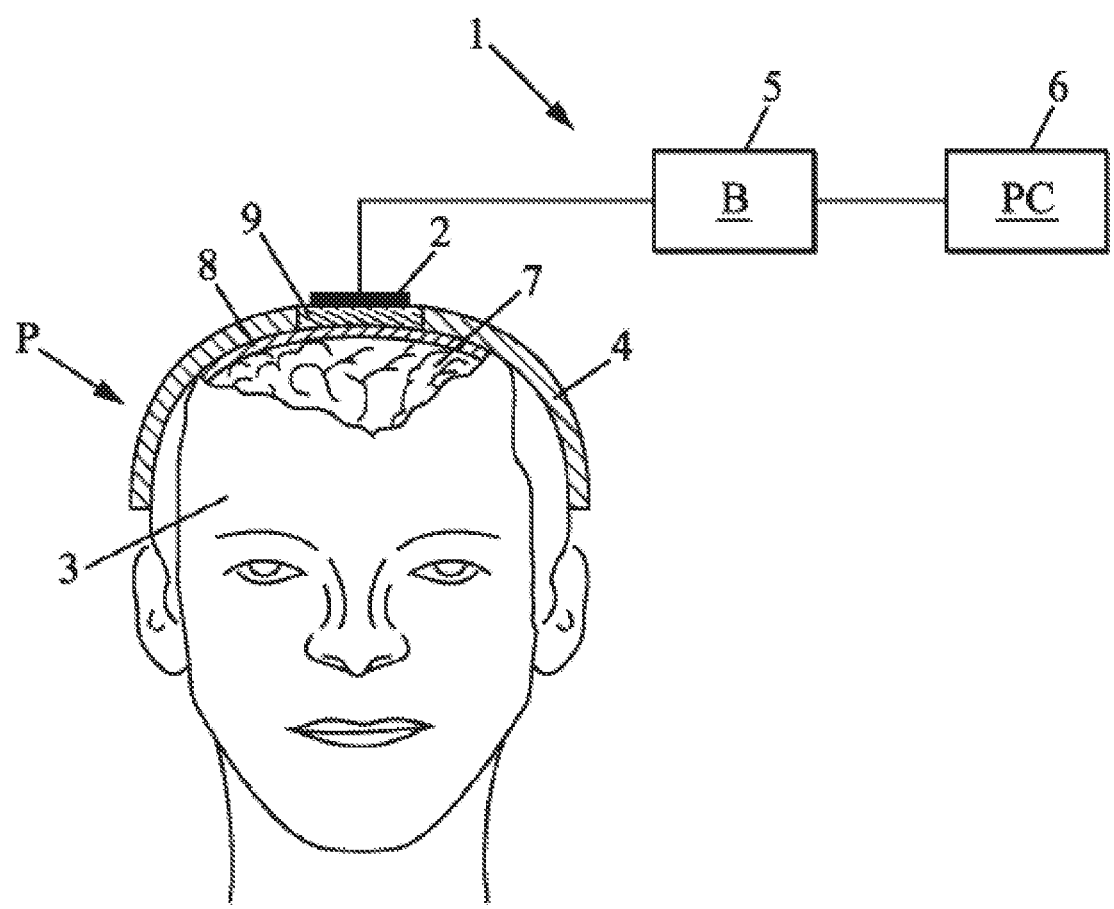
FIG. 1 is an overall schematic view of a sample ultrasonic wave generation mechanism practicing the invention, comprising an ultrasonic lens.

The mechanism 1 for generation of ultrasonic wave shown on FIG. 1 is capable of generating predetermined ultrasonic wave fields in a medium 3, for example the head of a patient P, or in another part of the body. The medium 3 comprises at least one aberrating barrier 8 (here the skull of the patient P) and at least one substantially homogeneous internal part 7 (here the brain of the patient P) masked by said aberrating barrier 8.

More generally, the substantially homogeneous medium 7 could be any tissue medium of a human patient or any other vertebrate, with tissue medium having substantially homogeneous characteristics for propagation of ultrasonic waves, whereas the aberrating barrier could be any other bone barrier. As an alternative example, the tissue medium could possibly be made up by the heart or the heart-lung system of the patient P, in which case the bone barrier would be made up by the thoracic cage.

The mechanism 1 is intended to generate ultrasonic waves in the brain 7 of the patient P (or more generally in the internal part 7 of the medium 3) at frequencies for example of order 0.1 to 10 MHz, in particular from 0.2 to 3 MHz, from the outside of the brain 8.

This generation of ultrasonic waves can be intended for example to:
- Make an ultrasonic image or series of images of the brain, whether it involves static or functional imaging, in particular Doppler imaging with which to view blood flow or thermal imaging with which to view heating caused by a hyperthermia treatment;
- And/or perform a hyperthermia treatment, in particular for destroying tumors, coagulating hemorrhages, and locally activating thermally activated medications;
- And/or locally open the blood-brain barrier in order to locally diffuse a medication previously injected intravenously;
- And/or activate/inhabit the brain by ultrasonic neuromodulation.

In these latter applications, it will be noted that obtaining an objective wave field is never in itself a therapeutic treatment, but a simple technical measure for focusing waves. The possible therapeutic treatment, selected by a physician, consists in the choice of the objective wave field, the intensity thereof, the length of application thereof, the number of applications of this objective wave field and their distribution over time.

In all cases, it is necessary to be able to generate, with the greatest precision possible, one or more predetermined objective ultrasonic wave field(s) in the brain 7 of the patient P, for example for focusing the ultrasonic waves emitted by an ultrasound probe 2 on one or more points of the brain, or for generating more complex wave fields. As shown in FIG. 4, the objective wave field can for example be a wave field focused on a focal spot F in the brain 7, or possibly several focal spots.

As shown in FIG. 1, the ultrasound probe 2 can for example be integrated in a helmet 4 positioned in a predetermined way on the head 3 of the patient P, or else said ultrasound probe 2 can be carried by any other known positioning system. In all cases, the ultrasound probe 2 is positioned outside of the skull 8 of the patient in a predetermined position.

An acoustic lens 9, here also called ultrasonic lens, also incorporated in the helmet 4, is interposed between the ultrasound probe 2 and the skull 8 of the patient P. A gel or liquid, which could be contained in a flexible pouch (not shown), can be interposed between the ultrasonic lens 9 and the skull 8 and or between the ultrasound probe 2 and the ultrasonic lens 9, so as to assure good transmission of ultrasonic waves. Here, this gel or liquid will be called external medium and considered as making up part of the propagation medium 3 of the ultrasonic waves.

The acoustic lens 9 can be made of any material in which the speed of compressive acoustic waves $c_1$ is different from the speed c of said waves in the brain (c is substantially the speed of sound in water, which is about 1480 m/s). The ultrasonic lens can for example be made of plastic, in particular polydimethylsiloxane, also called PDMS ($c_1$=1030 m/s), or polymethylpentene, known under the name TPX® ($c_1$=2090 m/s).

Some parts of the ultrasonic lens could be made of a material attenuating, reflecting or absorbing ultrasonic waves, in particular for locally attenuating the ultrasonic wave field made in the brain 7 or the skull 8, for example in areas not needing treatment or for limiting the heating of the skull.

The ultrasound probe 2 can be controlled by an electronic circuit 5(B) which itself could be controlled by a computer 6 (PC).

Figure 2:
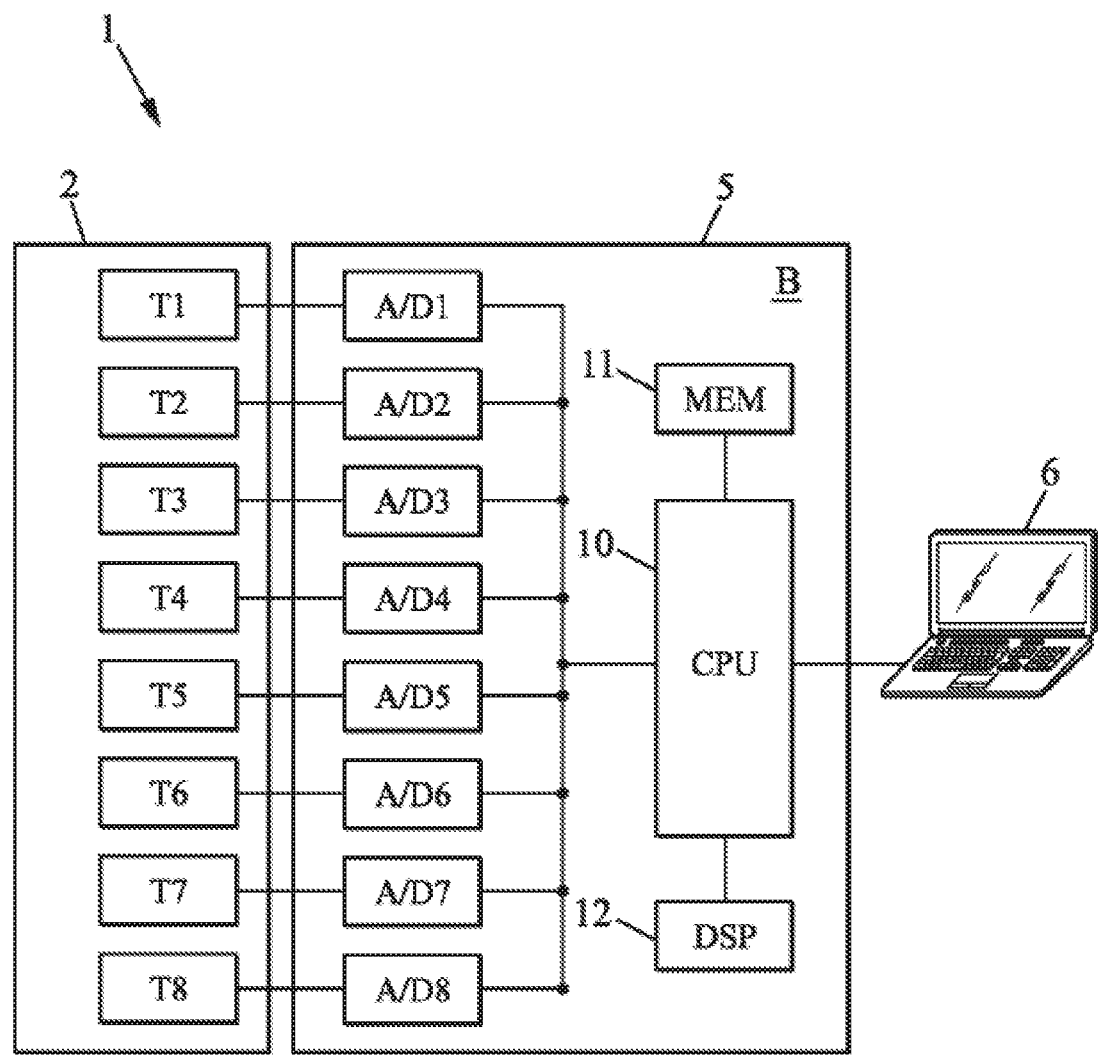
FIG. 2 is a functional drawing of the mechanism from FIG. 1.

As shown in FIG. 2, the ultrasound probe 2 can include one or more ultrasonic transducer(s) T1-T8. In the example shown there are eight of these transducers, but there could be more in particular in imaging applications or even fewer. Possibly, a single transducer T1 could be used, in particular when the ultrasonic wave only needs to be focused, in particular for purposes of treatment by thermal or mechanical effect. The ultrasound probe 2 could comprise transducers intended for ultrasonic imaging and others intended for hyperthermic treatment, as explained in the aforementioned document WO 2004/019784 A1.

As shown in FIG. 2, the electronic circuit 5 which controls the ultrasonic probe 2 can comprise:
- A central electronic unit 10 (CPU) controlled by the computer 7;
- At least one central memory 11 (MEN) connected to the central electronic unit 10;
- An analog-digital converter A/D1-A/D8 connected to each transducer T1-T8 and generally associated with a buffer memory (not shown);
- Possibly, a circuit specific for signal processing 12 (DSP);

To practice the mechanism previously described, the ultrasonic lens 9 is designed and produced such that the desired objective wave field can be obtained, for example by following the following steps:

(a) Determination of a Three-Dimensional Model of the Medium 3:

In advance, a three-dimensional model of the medium 3 is determined comprising a mapping of propagation properties of the ultrasonic waves in the medium.

This step generally comprises an imaging operation, in particular x-ray or MRI imaging, in particular in order to determine the bone density of the aberrating barrier 8 at each point, so the ultrasonic wave propagation parameters at each point can be determined, as explained in the aforementioned document WO 2004/019784 A1 (in particular mass density ρ, speed c of the ultrasonic waves and/or absorption T of said ultrasonic waves, at each point of the aberrating barrier 8).

The three-dimensional model can for example be loaded into the computer 6. A user can position the desired ultrasonic wave field, for example the one or more focal spot(s) F, on the image of the medium 3 (FIG. 4). This positioning can for example be done by viewing a lesion to be treated or other area of interest on the image of the medium 3 and by locating this area on the image using the user interface of the computer 6 (for example mouse, touchscreen or other). In the following, in the interest of simplicity, "the area of interest F" will be referred to for designating one or more focal spots or one or more complex objective wave field areas.

(b) Simulation:

The propagation of an ultrasonic wave through the aberrating barrier can be simulated from the aforementioned three-dimensional model for next determining the delays or phase shifts which will have to be induced by the lens, and then deducing from that the shape to give to the lens. This step can be done by the aforementioned computer 6 or another computer.

This simulation step can comprise the following substeps:

(b1) Determination of the Arrival Times on a Control Surface (S1-S'1):

As shown in S1 and S'1 on FIG. 3, it is possible to determine the arrival times $t_0(x,y)$ of a predetermined ultrasonic wave 13 emitted by an ultrasound probe 2, a different control points M(x,y), preferably belonging to a single control surface 14 disposed between the probe 2 and the aforementioned area of interest F. This control surface 14 is located between the aberrating barrier 8 and the ultrasound probe 2 at the position which the aforementioned acoustic lens 9 should occupy. The control surface 14 can for example be a plane XY where the axes X, Y are perpendicular to the Z axis disposed in the direction of the depth. This control surface could be any other flat or curved surface.

These arrival times $t_0(x,y)$ are easily determined by the computer 6 or other (up to an arbitrary constant time $T'_0$ common to the entire control surface 14), because the external part of the medium (outside of the aberrating barrier) is considered as homogeneous for the propagation of ultrasonic waves.

In the simple and the most common case where the probe is spherical with radius R, this determination can be done very simply in the form:

$$t_0(x,y)=T'_0-d(M)/c \qquad (2)$$

where:—d(M) is the distance between the control point M(x,y) and the center of curvature the probe;

c is the speed of the ultrasonic wave in the external part of the medium 3.

More generally, the arrival times $t_0(x,y)$ can be determined by calculation of the ultrasonic wave propagation between the probe and the control points or by any other known wave propagation method, which is simple in an homogeneous medium (propagation can then be done in a simplified model allowing an analytic calculation).

The arrival times $t_0(x,y)$ will hereafter be called first arrival times.

(b2) Simulation of the Back Propagation of the Desired Ultrasonic Wave in the Area of Interest in the Three-Dimensional Model (S2):

As shown in S2 in FIG. 3, during this substep b2, a back propagation of the predetermined objective ultrasonic wave field in the medium 3 is simulated from the area of interest F in the medium 3 to the aforementioned control surface 14.

This simulation can be done for example by the computer 6, for example by using a wave equation such as equation. (1) below:

$$\left(1+\tau(\vec{r})\frac{\partial}{\partial t}\cdot\right)\left[\rho(\vec{r})\nabla\cdot\left(\frac{1}{\rho(\vec{r})}\nabla\ p(\vec{r},t)\right)\right]-\frac{1}{c(\vec{r})^2}\frac{\partial^2\ p(\vec{r},t)}{\partial t^2}=S(\vec{r},t), \qquad (1)$$

Where $\vec{r}$ designates a position vector for the point considered; p designates the pressure; and S designates the ultrasonic signals generated by an ultrasonic source which could be present at the point considered.

The propagation of ultrasonic waves in the aberrating barrier 8 and the internal part 7 can be simulated in the computer by finite differences, by discretizing the equation (1) above. The simulation can also be done by finite elements, or by an impulse diffraction method, or any other known method.

(b3) Determination of the Second Arrival Times on the Control Surface 14 (S'2):

As shown in S'2 in FIG. 3, the arrival times $t_1(x,y)$ of the ultrasonic wave 13c, 13b representative of the back propagation of the predetermined objective wave field can be determined at said control points M(x,y) belonging to the control surface 14 with the aforementioned simulation.

The arrival times $t_1(x,y)$ are counted for example from the instant of emission of the ultrasonic wave 13c in said area F, where x and y are respectively the coordinates on the axes X, Y of each control point M considered. The arrival times $t_1(x,y)$ are hereafter be called second arrival times.

(b4) Determination of the Delay Law of the Lens (S3):

As shown in S3 on FIG. 3, the delay law $\Delta t(x,y)$ is determined at various control points M(x,y), equal to the sum of the first arrival times $t_0(x,y)$ and second arrival times $t_1(x,y)$.

(c) Calculation of the Ultrasonic Lens (S4):

Starting from the aforementioned delay law $\Delta t(x,y)$, the computer 6 or other next calculates the profile of the ultrasonic lens 9 which, when it is interposed between the ultrasound probe 2 and the aberrating barrier a, is able to add said delay $\Delta t(x,y)$, such that when the ultrasound probe 2 emits said predetermined ultrasonic wave 13a, said predetermined wave after traversing the lens and then the aberrating barrier produces the predetermined ultrasonic wave field in the area of interest.

More precisely, a thickness e of the ultrasonic lens 9 can be calculated at each point of said lens corresponding to a control point M(x,y) of the control surface 14, such that the thickness e of the lens introduces an ultrasonic wave propagation time correction corresponding to said delay law modulo the period T=1/f of the ultrasonic wave (where f is the central frequency of the ultrasonic wave) and/or up to an arbitrary constant time $T_0$ common to the entire control surface.

For example, the ultrasonic lens thickness e(x,y) can be calculated at each point L(x,y) of the lens corresponding to a control point M(x,y), with the following formula (3):

$$e(x,y)=\Delta t(x,y)/(1/c-1/c_1)+e_0 \qquad (3).$$

The constant $e_0$ is a real number such that e(x,y) has a has a value at each point of the lens that is positive and minimal.

In the case of the emission of a monochromatic wave, the ultrasonic lens thickness e(x,y) can be calculated at each point L(x,y) of the lens corresponding to a control point M(x,y), with the following formula (4):

$$e(x,y)=\Delta t(x,y)/(1/c-1/c_1)+e_0, \text{modulo} T/(1/c-1/c) \quad (4).$$

Modulo $T/(1/c-1/c_1)$ means that $e(x,y)=\Delta t(x,y)/(1/c-1/c_1)+e_0+n \cdot T/(1/c-1/c_1)$, where n is a positive or negative integer such that e(x,y) has a positive value. The integer n can be common to the entire lens 9 (simple lens) or could be different according to the regions the lens 9 (Fresnel lens).

It will be noted that the lens calculation step (c) can consider at least travel times of the predetermined ultrasonic wave in the ultrasonic lens 9 and angles of incidence of said predetermined ultrasonic wave with the surface of the ultrasonic lens 9. The lens calculation step (c) can also consider the entire propagation of said predetermined ultrasonic wave, including echoes between the ultrasound probe 2, the ultrasonic lens 9 and the aberrating barrier 8. The lens calculation step (c) can be done iteratively in order to optimize the ultrasonic energy transmission yield in the predetermined area F, using an analytic or numerical model.

(d) Implementation of the Ultrasonic Lens (S5):

Once the profile of the lens 9 for the patient P (or more generally for a given application) is calculated, it can be produced, preferably by a rapid production method.

In particular one of the commonly used production methods for rapid prototyping can be used, for example:

Three-dimensional printing of the lens 9;

Numerically controlled machining of a block of material in order to form the lens 9;

A process with two substeps comprising:

(d1) A substep of mold production (not shown) done by a method chosen among three-dimensional printing of the mold and numerically controlled machining of a block of material for forming the mold;

(d2) A substep of molding in which said lens 9 is molded in said mold.

(e) Use:

Once the lens 9 is produced, it can be attached in the aforementioned helmet 4 or other support, and thus positioned in the predetermined position that it must occupy on the skull 8 of the patient P. An operator can then send the predetermined wave 13a from the ultrasound probe 2 through the ultrasonic lens 9.

As shown in FIG. 4, the lens 9 introduces aberrations which form the wavefront 13b upstream from the skull 8, such that after passage through the skull 8 or another aberrating barrier, the wavefront 13c corresponds to the aforementioned theoretical wave 13. Thus the objective wave field results, for example of focusing in the focal spot F.

The wave thus sent, into the brain or other internal part 7 can serve to treat the area of interest F as previously explained. Further, the brain or another internal part 7 at least in the neighborhood around the area of interest F could be imaged, when the ultrasound probe 2 comprises ultrasonic transducers for imaging, because the ultrasonic lens 9 compensates the aberrations due to the skull or other aberrating barrier 8 both during transmitting and receiving.

The method according to the invention can further comprise an optional step (f) of verification of the positioning of the device, during which ultrasonic echoes which are reflected on said aberrating barrier are recorded on the ultrasound probe and the echoes are compared to the same reflected signal simulated by using the aforementioned model of the medium 3.

In all scenarios, the lens 9 can be produced in a material having mechanical characteristics (in particular hardness), and therefore acoustic wave propagation characteristics, modifiable by exposure to a predetermined radiation.

The predetermined radiation can for example be ultraviolet radiation.

The material in question can for example be polydimethylsiloxane (PDMS) or polyvinylmethylsiloxane (PVMS), which harden under ultraviolet radiation.

In this case, during lens calculation step (c), the lens 9 can be calculated by determining local mechanical characteristics of acoustic wave propagation in said lens 9 with which to achieve the desired objective wave field. These mechanical properties can be determined in addition to the shape of the lens 9, or as a variant, the objective wave field could be obtained just by local variations of local propagation characteristics of the lens 9.

During the step (d) of implementation of the lens 9, said lens is locally exposed to said predetermined radiation for obtaining the local mechanical properties of acoustic wave propagation determined in lens calculation step (c).

The invention claimed is:

1. A production method for implementing an ultrasonic lens for purposes of insonification of a medium comprising at least one aberrating barrier and a substantially homogeneous internal part masked by said aberrating barrier, in order to obtain a predetermined objective ultrasonic wave field in at least one predetermined area belonging to said internal part, by having said ultrasonic waves sent by an ultrasound probe placed in a position predetermined relative to said medium on the other side of said aberrating barrier from said internal part, the production method comprising at least one lens calculation step during which an ultrasonic lens is calculated, using a model of the medium comprising a mapping of ultrasonic wave propagation properties obtained from actual imaging of the medium, that is suited, when it is interposed between the ultrasound probe and the aberrating barrier, for generating aberrations such that when the ultrasound probe sends a predetermined ultrasonic wave, said predetermined wave generates said predetermined objective ultrasonic wave field in said predetermined area.

2. The production method according to claim 1, further comprising a step of implementation of the lens calculated in the lens calculation step.

3. The production method according to claim 2, wherein the lens implementation step is done by a method chosen among three-dimensional printing of the lens and digitally controlled machining of at least one block of material for forming the lens.

4. The production method according to claim 2, wherein the lens implementation step comprises the following substeps:

a substep of mold implementation done by a method chosen among three-dimensional printing of said at least one mold and numerically controlled machining of at least one block of material for forming said at least one mold;

a substep of molding in which said lens or at least one component of said lens is molded in said at least one mold.

5. The production method according to claim 1, wherein the lens calculation step is preceded by an imaging step during which said mapping is done.

6. The production method according to claim 5, wherein the imaging step is done by x-ray or MRI imaging.

7. The production method according to claim 6, wherein said cartography is done from bone density measurements.

8. The production method according to claim 1, wherein the lens calculation step is preceded by a simulation step during which:
- propagation in the medium of the predetermined ultrasonic wave from the ultrasound probe disposed at said predetermined position to a chosen position of the lens is calculated, and the first arrival times $t_0(x,y)$ of said predetermined ultrasonic wave to said chosen lens position are determined;
- back-propagation in the medium of said predetermined objective ultrasonic wave field from the predetermined area to said chosen lens position is simulated;
- second arrival times $t_0(x,y)$ of said back-propagation of said predetermined objective ultrasonic wave field to said chosen lens position are determined;
- a delay law $\Delta t(x,y)$ at said chosen lens position equal to the sum of the first arrival times $t_0(x,y)$ and second arrival times $t_0(x,y)$ is determined;
- And during the lens calculation step, the ultrasonic lens is calculated using said delay law $\Delta t(x,y)$, so that when the ultrasound probe sends said predetermined ultrasonic wave through said ultrasonic lens, said predetermined wave reproduces the objective wave field in said area F after passing through said aberrating barrier.

9. The production method according to claim 8, wherein the first arrival times $t_0(x,y)$ and the second arrival times $t_1(x,y)$ are determined at different control points $M(x,y)$ belonging to a predetermined control surface located at said chosen lens location.

10. The production method according to claim 9, wherein the control surface is located between the ultrasound probe and the aberrating barrier.

11. The production method according to claim 9, wherein at the lens calculation step, an ultrasonic lens thickness $e(x,y)$ is calculated at each point $L(x,y)$ of the lens corresponding to a control point $M(x,y)$ with the following formula:

$$e(x,y)=\Delta t(x,y)/(1/c-1/c_1)+e_0$$

where: c is the speed of the ultrasonic wave in the medium outside of the aberrating barrier;
$c_1$ is the speed of the ultrasonic wave in the lens;
$e_0$ is a real number such that $e(x,y)$ has a has a value at each point of the lens that is positive and greater than a predetermined thickness.

12. The production method according to claim 9, wherein the ultrasonic wave is monochromatic and at the lens calculation step (c), a lens thickness $e(x,y)$ is calculated at each point $L(x,y)$ of the lens corresponding to a control point $M(x,y)$ with the following formula:

$$e(x,y)=\Delta t(x,y)/(1/c-1/c_1)+e_0, \text{modulo} T/(1/c-1/c_1)$$

where: c is the speed of the ultrasonic wave in the medium outside of the aberrating barrier;
$c_1$ is the speed of the ultrasonic wave in the lens;
$e_0$ is a real number such that $e(x,y)$ has a has a value at each point of the lens that is positive and greater than a predetermined thickness;
T is the period of the ultrasonic wave.

13. The production method according to claim 8, wherein at substep, the arrival times $t_0(x,y)$ can be determined by simulating propagation of said predetermined ultrasonic wave in a simplified model allowing an analytic calculation.

14. The production method according to claim 1, wherein the lens calculation step considers travel times of said predetermined ultrasonic wave in the ultrasonic lens and angles of incidence of said predetermined ultrasonic wave at the surface of the ultrasonic lens.

15. The production method according to claim 1, wherein the lens calculation step (e) considers the entire propagation of said predetermined ultrasonic wave, including echoes between the ultrasound probe, the ultrasonic lens and the aberrating barrier.

16. The production method according to claim 1, wherein the lens calculation step is done iteratively in order to optimize the ultrasonic energy transmission yield in the predetermined area, using an analytic or numerical model.

17. The production method according to claim 1, wherein the lens is made of a material having acoustic wave propagation properties modifiable by exposure to a predetermined radiation,
- during lens calculation step, the lens is calculated by determining local mechanical characteristics of acoustic wave propagation in said lens;
- and the method comprises a step of implementation of the lens during which said lens is locally exposed to said predetermined radiation for obtaining the local mechanical properties of acoustic wave propagation determined in lens calculation step.

* * * * *